(12) United States Patent
Di Nardo et al.

(10) Patent No.: US 8,100,861 B2
(45) Date of Patent: Jan. 24, 2012

(54) SEAL FOR TROCAR

(75) Inventors: Silvio Di Nardo, St. Gallen (CH); Bruno Nyffenegger, Balgach (CH)

(73) Assignee: Oertli-Instrumente AG, Berneck (CH)

( * ) Notice: Subject to any disclaimer, the term of this patent is extended or adjusted under 35 U.S.C. 154(b) by 46 days.

(21) Appl. No.: 12/402,809

(22) Filed: Mar. 12, 2009

(65) Prior Publication Data

US 2009/0234292 A1 Sep. 17, 2009

(30) Foreign Application Priority Data

Mar. 17, 2008 (CH) ........................................ 0394/08

(51) Int. Cl.
*A61M 5/178* (2006.01)
(52) U.S. Cl. .................................. 604/167.04
(58) Field of Classification Search ............. 604/164.01, 604/167.01, 167.03, 167.04; 606/107, 166
See application file for complete search history.

(56) References Cited

U.S. PATENT DOCUMENTS

| | | | | |
|---|---|---|---|---|
| 3,659,607 A * | 5/1972 | Banko | ............................ | 606/169 |
| 5,380,288 A | 1/1995 | Hart et al. | | |
| 5,549,565 A * | 8/1996 | Ryan et al. | ................ | 604/167.03 |
| 5,613,954 A * | 3/1997 | Nelson et al. | ............. | 604/167.03 |
| 5,865,807 A | 2/1999 | Blake, III | | |
| 5,871,471 A * | 2/1999 | Ryan et al. | ................ | 604/167.03 |
| 5,993,471 A | 11/1999 | Riza et al. | | |
| 6,123,689 A | 9/2000 | To et al. | | |
| 7,608,082 B2 * | 10/2009 | Cuevas et al. | .................. | 606/108 |
| 2008/0033462 A1 * | 2/2008 | Di Nardo et al. | .............. | 606/166 |
| 2009/0234293 A1 * | 9/2009 | Albrecht et al. | ......... | 604/167.02 |
| 2010/0076381 A1 * | 3/2010 | Simonsen | ................ | 604/167.02 |

FOREIGN PATENT DOCUMENTS

| | | |
|---|---|---|
| EP | 0 564 373 A1 | 10/1993 |
| EP | 1 886 653 A1 | 2/2008 |
| FR | 2 710 270 A1 | 3/1995 |
| FR | 2 727 849 A1 | 6/1996 |

* cited by examiner

*Primary Examiner* — Nicholas Lucchesi
*Assistant Examiner* — Aarti B Berdichevsky
(74) *Attorney, Agent, or Firm* — The Webb Law Firm

(57) ABSTRACT

A seal for use in a trocar, particularly for a trocar for eye surgery, having a seal element, with a seal opening, and an instrument opening. The instrument opening extends along a center axis on both sides of the seal element all the way through the seal. The seal also has a clamp element for establishing a form-fit connection to an instrument that is inserted at least partially into the instrument opening and through the seal opening.

14 Claims, 4 Drawing Sheets

SEAL FOR TROCAR

BACKGROUND OF THE INVENTION

1) Field of the Invention

The present invention relates to a seal for a trocar and to a trocar with a seal.

2) Description of the Related Art

Trocars with seals, or seals for trocars, are known from the prior art and are used by specialists in a large number of operations on the eye.

In most cases, three trocars are normally used in an operation on the eye. Each trocar, also referred to as a guide tube, is introduced into the eye in such a way that the tip of the trocar extends into the vitreous body (corpus vitreum) of the eye, while the opposite end is available as an attachment. The eye in most cases has to be supplied with an infusion, which is done by way of what is called the infusion trocar. Two further trocars are also used in most cases. Suitable instruments or lighting devices can then be advanced to the eye through these further trocars. These further trocars are also referred to as instrument trocars or illuminating trocars.

A seal has to be provided between the trocars and the inserted instrument in order to avoid escape of a fluid when the trocar is in place. For example, the company DORC has started fitting a kind of cap on the flange of the trocar, which cap provides the seal between trocar and instrument. However, such a cap has the disadvantage of increasing the external diameter of the trocar.

U.S. Pat. No. 5,865,807 discloses a further seal that can be arranged in the inside of a trocar. This seal has two sealing locations. This is advantageous as regards the quality of the seal but has the disadvantage that the instruments have to be pushed in the longitudinal direction through two seals, causing greater forces to act on the eye.

SUMMARY OF THE INVENTION

Starting out from this prior art, it is an object of the invention to make available a trocar seal that overcomes the disadvantages of the prior art. Moreover, a trocar is to be made available which permits easy connection of an instrument or infusion attachment to the trocar.

This object is achieved by a trocar seal according to the present invention. Advantageous embodiments of the invention are set forth in the dependent claims.

Accordingly, such a seal comprises a seal element, with a seal opening, and an instrument opening, which instrument opening extends along a centre axis on both sides of the seal element all the way through the seal, and the seal also comprises a clamp element for establishing a form-fit connection to an instrument that is inserted at least partially into the instrument opening and through the seal opening.

An advantageous trocar according to the invention has a seal of this kind fitted in it. By means of an outer circumferential bead on the seal, a form-fit connection can advantageously be achieved with a complementary recess in the inside wall of the trocar, such that insertion and extraction forces applied to this system by an instrument do not lead to a displacement of the seal in the trocar, although a reliable connection of the instrument or infusion attachment to the trocar is permitted.

Further advantageous embodiments are characterized in the dependent claims.

BRIEF DESCRIPTION OF THE DRAWINGS

Examples of preferred embodiments are described in more detail below with reference to the drawing, in which.

DETAILED DESCRIPTION OF THE INVENTION

Possible illustrative embodiments are described with reference to the drawings. The drawings and the description show preferred illustrative embodiments and should not be interpreted in such a way as to limit the invention, which is defined by the claims.

Figure 1:
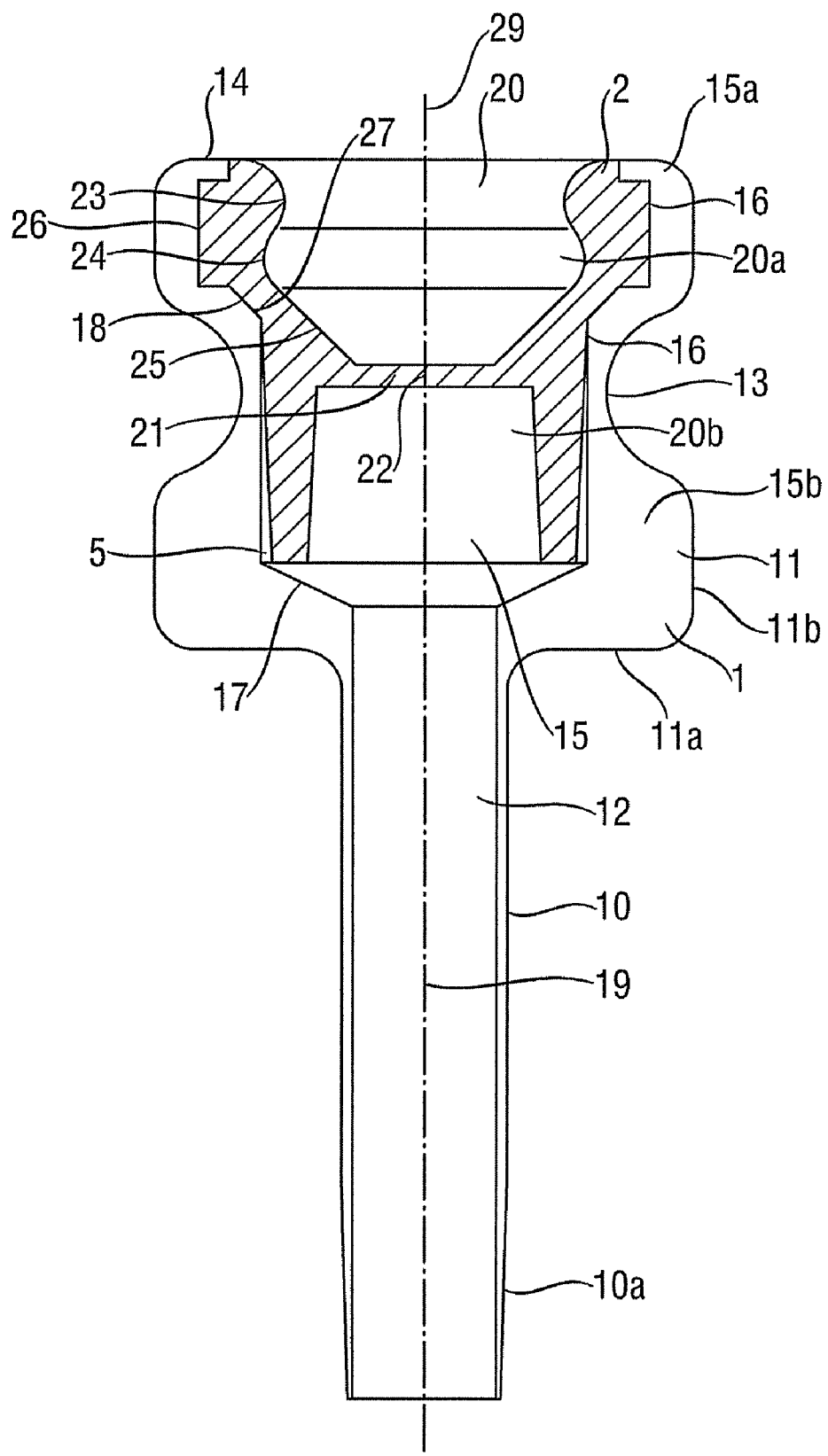
FIG. 1 shows a cross-sectional view of a trocar with a seal according to the invention.

FIG. 1 shows the cross-sectional view of a trocar 1 with a seal 2. Such a trocar is used in eye surgery.

The trocar 1 principally comprises a cannula 10, and a flange 11 formed integrally on this cannula 10. The cannula 10 has a smaller diameter than the flange 11. The cannula 10 is inserted into the eye via an incision in the eye. The flange 11 comes to lie in such a way that its surface 11a extending perpendicular to the cannula comes to lie on the surface of the eye. The transition between cannula 10 and flange 11 is preferably rounded.

Both the cannula 10 and the flange 11 are preferably substantially cylindrical and extend along a centre axis 19. The outer contour of the cannula 10 is conical in the lower area 10a, which is introduced first into the eye, thus ensuring that the trocar 1 is inserted as easily and smoothly as possible.

A cylindrical opening 12 extends through the cannula 10 along the centre axis 19 thereof. In the area of the flange 11, the cylindrical opening 12 merges into a receiving opening 15, which is of greater diameter and extends all the way through the flange 11. An opening 12, 15 is thus created that extends through the entire trocar 1.

The receiving opening 15 serves to receive the seal 2 described below. For this purpose, the receiving opening 15 has, in its distal area, a circumferential recess 16 which extends into the flange 11 near the top face 14 of the receiving opening 15. In the upper area 15a before the recess 16, the receiving opening has a greater diameter than in the proximal, lower area 15b directed towards the cannula 10. The receiving opening 15 also has a greater diameter than the opening 12 extending through the cannula 10. The transition between the receiving opening 15 and the opening 12 is designed with a bevel 17. A further bevel 18 is also provided at the transition from the recess 16 to the lower area 15b. The recess 16 can also be configured differently, provided that it establishes a connection, preferably a form-fit connection or, if appropriate, a force-fit connection to the seal 2. The function of the recess 16 is therefore to hold the seal 2 in the trocar 1.

The trocar 1 further comprises an outer circumferential groove 13, which is here arranged in the area of the flange 11. The groove 13 is formed into the circumferential surface 11b of the flange 11. The circumferential groove 13 can be easily gripped by forceps, such that the trocar 1 can be suitably placed in the eye or removed again.

The seal 2 is likewise shown in a cross-sectional view in FIG. 1. The seal 2 comprises an instrument opening 20 that extends along a centre axis 29 of the seal 2 and essentially through the entire seal 2. The centre axis 29 of the instrument opening 20 is flush with the centre axis of the trocar 1 here.

The instrument opening 20 serves basically for guiding the instruments that are to be guided through the trocar 1. The seal 2 further comprises a seal membrane 21 with a seal opening 22. The seal membrane 21 extends perpendicular to the centre axis 29 and divides the instrument opening 20 into an upper section 20a and a lower section 20b.

Figure 4A:
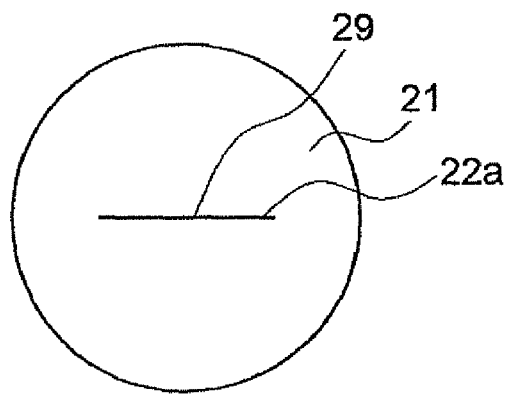
FIGS. 4a and 4b show a schematic plan view of the seal membrane of the seal.

The seal opening 22 is designed as a slit 22a, formed radially with respect to the centre axis 29, in the seal membrane 21. The radially formed slit 22a is shown in FIG. 4a, which shows a schematic detail of the seal membrane 21 in plan view. The slit 22a runs in two radial lengths from the centre axis 29 to cover, for example, ⅔ of the diameter of the instrument opening 20. The slit and the seal membrane 21 are dimensioned in such a way that they can withstand a pressure of up to 0.1 bar or, in another illustrative embodiment, of 0.2 bar, which acts on the seal membrane 21 from the lower section 20b, and can thus maintain a sealing action. In the case of use of the trocar 1, said pressure is an intraocular pressure. In other words, this means that the seal membrane 21 and the seal opening 22 can also seal off the opening through the entire trocar 1 even when there is no instrument guided through the trocar 1 and through the seal 2.

Figure 4B:
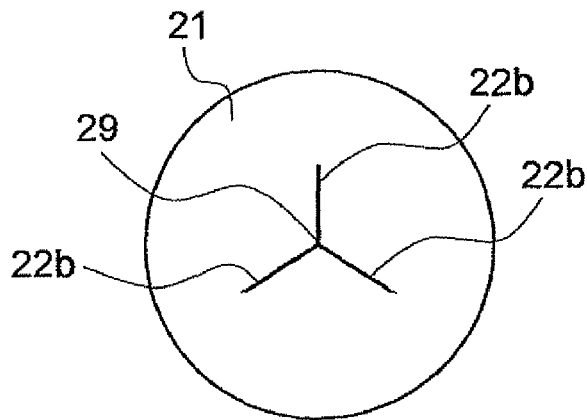

In other embodiments, for example as shown in FIG. 4b, three slits 22b run in the radial direction from the centre axis 29. The slits are arranged at an angle of 120°, for example. Other arrangements of the slits are also conceivable.

The upper section 20a of the instrument opening 20 also comprises a clamp element 23. The clamp element 23 is designed in such a way that it can establish a releasable form-fit connection to an instrument that is to be inserted, such that an axial displacement of the instrument relative to the trocar 1 can be avoided. For this purpose, the clamp element 23 extends from the top surface of the instrument opening 20 into the instrument opening 20, such that the diameter thereof is reduced in the area of the clamp element 23. It can generally be said, accordingly, that the seal 2 serves not only as a seal element but also as a securing element or clamp element.

In the present illustrative embodiment, the clamp element 23 is designed as a convex circumferential clamping bead. The clamping bead forms the first part of the upper section 20a of the instrument opening 20. After the clamping bead, the surface of the instrument opening 20 merges into a concave rounding 24. The concave rounding 24 is adjoined by a bevel 25, which merges into the seal membrane 21. The bevel 25 reduces the diameter of the instrument opening 20 towards the seal membrane 21.

It is advantageous that the clamp element 23 is arranged opposite the upper area 15a and the recess 16 is such a way that radially acting forces, during insertion or withdrawal of an instrument, ensure that there is no longitudinal displacement of the seal 2 in the trocar 1.

In other illustrative embodiments, it is conceivable, for example, for the clamping bead 23 to be divided into sections. The upper section 20a can also be designated as coupling section or snap-in section. Moreover, it is also conceivable to designate the clamping bead as snap-in fastener.

During insertion of an instrument 3, the clamp element 23 is slightly deformed by parts of the instrument 3. That is to say, in the case of a fixed recess 16, the clamping bead 23 can be slightly compressed upon insertion of the instrument, so as to allow the instrument to be inserted. The instrument 3 has a section designed complementary to the clamp element 23. That is to say, the complementary section of the instrument 3 has, when seen in a cross-sectional view, the shape that is the diametrical opposite of the corresponding section of the clamp element 23. As soon as the instrument 3 has been advanced such that it has reached the desired depth of insertion, the clamp element 23 recovers its original shape. The clamping bead 23 then engages in the complementary section, which in this case has a corresponding depression or groove. This engagement or latching has the effect that a form-fit connection can be established between the instrument 3 and the seal 2. The complementary section can also be designated as coupling section 34.

Generally, a form-fit connection is understood as a connection of two elements in which parts of one element engage in sections of complementary shape of the other element, such that a relative movement of the two elements can be prevented up to a point where a certain force is applied.

In an alternative embodiment, the clamp element 23 could also be designed as a groove, in which case the instrument then comprises the complementary bead.

The lower section 20b of the instrument opening 20 extends slightly conically from the seal membrane 21, such that the internal diameter of the instrument opening 20 becomes greater away from the seal membrane 21, seen in the direction of the centre axis 29. The instrument opening 20 in this lower section 20b can also be designated as membrane receiver, since the seal membrane 21 comes to lie in this area when an instrument is guided through. The outer wall in this section also extends slightly conically in the direction from the seal membrane, as a result of which a small gap 5 forms between the wall of the receiving opening 15 and the outer wall of the seal 2. The gap 5 has basically two functions. When fitting the seal 2 in the trocar 1, the insertion of the seal 2 is made easier since in this area there is no contact between seal 2 and trocar 1, which means that no frictional forces arise. Upon insertion of an instrument through the seal 2, the seal is able to deform outwards, that is to say towards the trocar 1. In this way, the surgeon is able to insert the instrument with less axial force being applied.

On the outside, the seal 2 has a circumferential flange 26 in the upper area. The circumferential flange 26 is designed in such a way that it is complementary to the recess 16 and is in engagement with the latter. The seal also has an outer bevel 27, which is in engagement with a bevel 18 of the opening 15. The connection between flange 26 and recess 16 permits a good connection between seal 2 and trocar 1. By virtue of the design, axial forces and also radial forces can be compensated. To put it another way, the shape of the outside of the seal 2 in the upper area 20a is substantially congruent to the shape of the inside wall of the receiving opening 15.

The seal 2 is preferably made from a silicone polymer. The silicone polymer preferably has a Shore hardness in the range of Shore 70 to Shore 80. Other Shore hardness values are also conceivable, however. It is also possible to use other plastics, in particular thermoplastic elastomers (TPE), for the seal. The trocar 1 is made of metal, for example instrument-grade steel, titanium or a titanium alloy, or of a plastic with a sufficient stiffness. The materials used must be biocompatible.

The seal 2 is preferably inserted into the receiving opening 15 along the centre axis 19. By virtue of the above-described shape of the seal, a form-fit connection is established between the seal 2 and the trocar 1. In alternative illustrative embodiments, it is also conceivable for the seal 2 to be adhesively bonded or to be injected directly into the receiving opening 15 by a plastics injection-moulding technique. For example, a two-component injection-moulding technique can be used here. Alternatively, the trocar 1 and the seal 2 can also be designed in one piece.

As is shown, the seal 2 is arranged fully within the trocar 1. This is advantageous since, in contrast to other sealing arrangements, the diameter of the trocar 1 is not increased.

The ophthalmic surgeon therefore has a better view of the eye that is to be operated on, and he is better able to handle the trocars.

Figure 2:
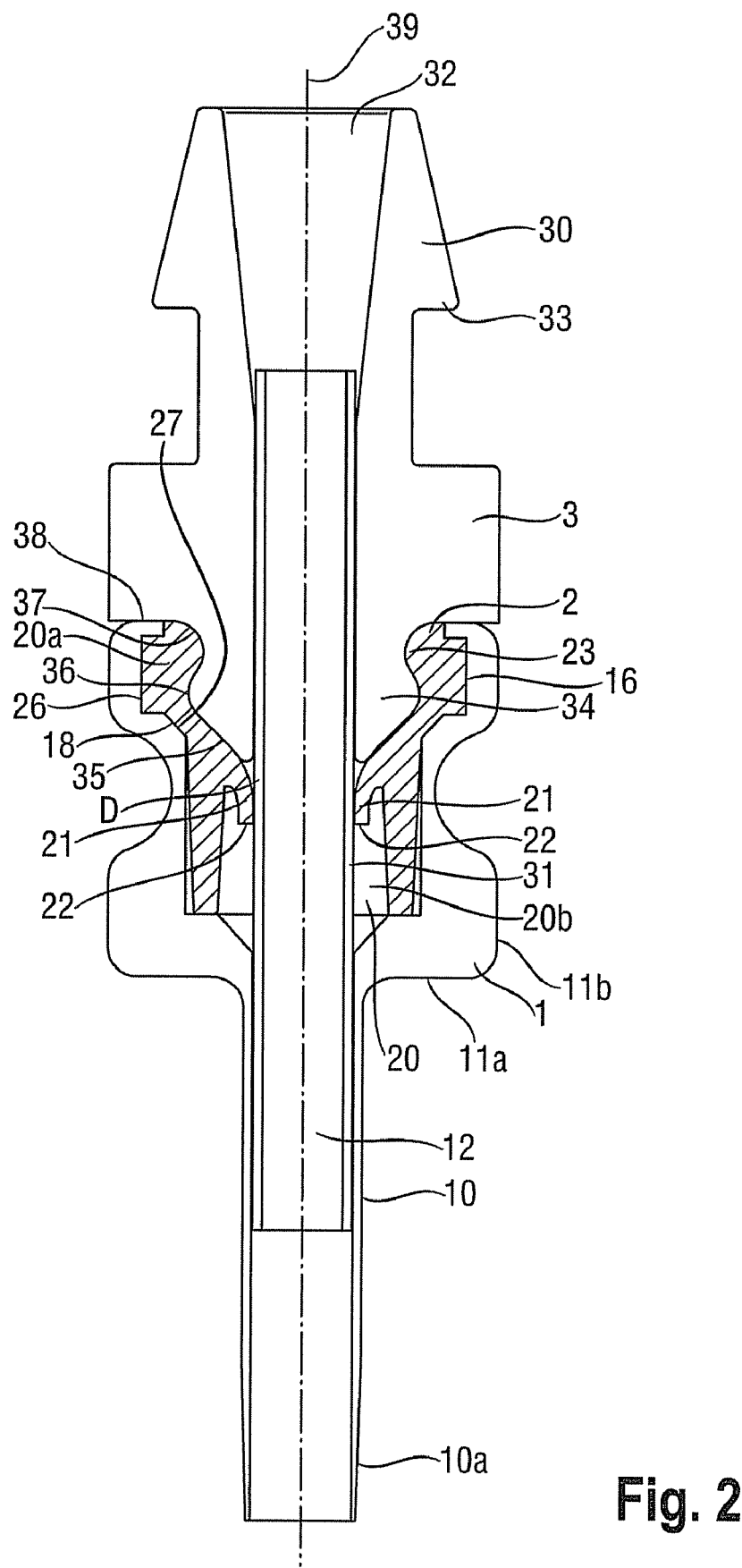
FIG. 2 shows a cross-sectional view of the trocar with the seal according to FIG. 1, and with an infusion attachment.

FIG. 2 shows the trocar 1 and the seal 2, with an infusion attachment 3 connected to the trocar 1 and to the seal 2. The infusion attachment 3 in this case comprises a coupling piece 30 and an attachment tube 31.

The coupling piece 30 comprises a through-opening 32, a hose attachment section 33 and a coupling section 34. The through-opening 32 serves to receive the attachment tube 31 and extends along a centre axis 39 all the way through the coupling piece 30. The attachment tube 31 protrudes beyond the coupling piece 30 in the axial direction.

The hose attachment section 33 serves to connect the coupling piece 30 to an infusion line and is designed accordingly.

The coupling section 34 has a design substantially complementary to the upper section 20a of the instrument opening 20. In the front area, the coupling section 34 has the shape of a cone 35. The cone 35 is adjoined by a convex rounding 36, which merges into a concave rounding 37. The concave rounding 37 adjoins the coupling section 34. As has been mentioned above, the coupling section 34 is adjoined by the hose attachment section 33. In the area directly adjoining the coupling section 34, the hose attachment section 33 has an abutment surface 38 extending perpendicular to the centre axis.

When the infusion attachment 3 is inserted into the trocar 1 and into the seal 2, the attachment tube 31 passes, in a first step, through the seal opening 22 in the seal membrane 21. A leaktight contact arises between seal opening 22 and attachment tube 31. The sealing location is designated by reference sign D. The seal membrane 21 is thus displaced into the membrane receiver or lower section 20b of the instrument opening 20.

In a second step, the cone 35 impacts the clamp element 23. The clamp element 23 is thus compressed in the radial direction, such that the infusion attachment 3 can be moved farther in the axial direction. The infusion attachment 3 is moved in the axial direction until the concave rounding 37 comes to lie at the level of the clamp element 23. In other words, this means that the clamp element 23 fills the concave rounding 37. A form-fit connection is thus established between the seal 2 and the infusion attachment 3. This form-fit connection can also be designated as snap-fit connection, since the coupling section 34 snaps into or latches in the upper section 20a or the coupling section. The form-fit, latched-in connection is particularly advantageous since in this way the infusion attachment is held firmly and stabilized in the trocar 1. By virtue of the congruent form of the two coupling sections 20a and 34, the connection is additionally stabilized with respect to transverse forces, which occur transverse to the centre axes.

When removing the infusion attachment 3, the tensile force has to be slightly increased, such that the clamp element 23 is again suitably compressed. It is important that the holding forces upon release of the coupling section 34 from the concave rounding or circumferential groove 24 are smaller than the forces that act between the recess 16 and the upper section 20a of the seal 2.

Figure 3:
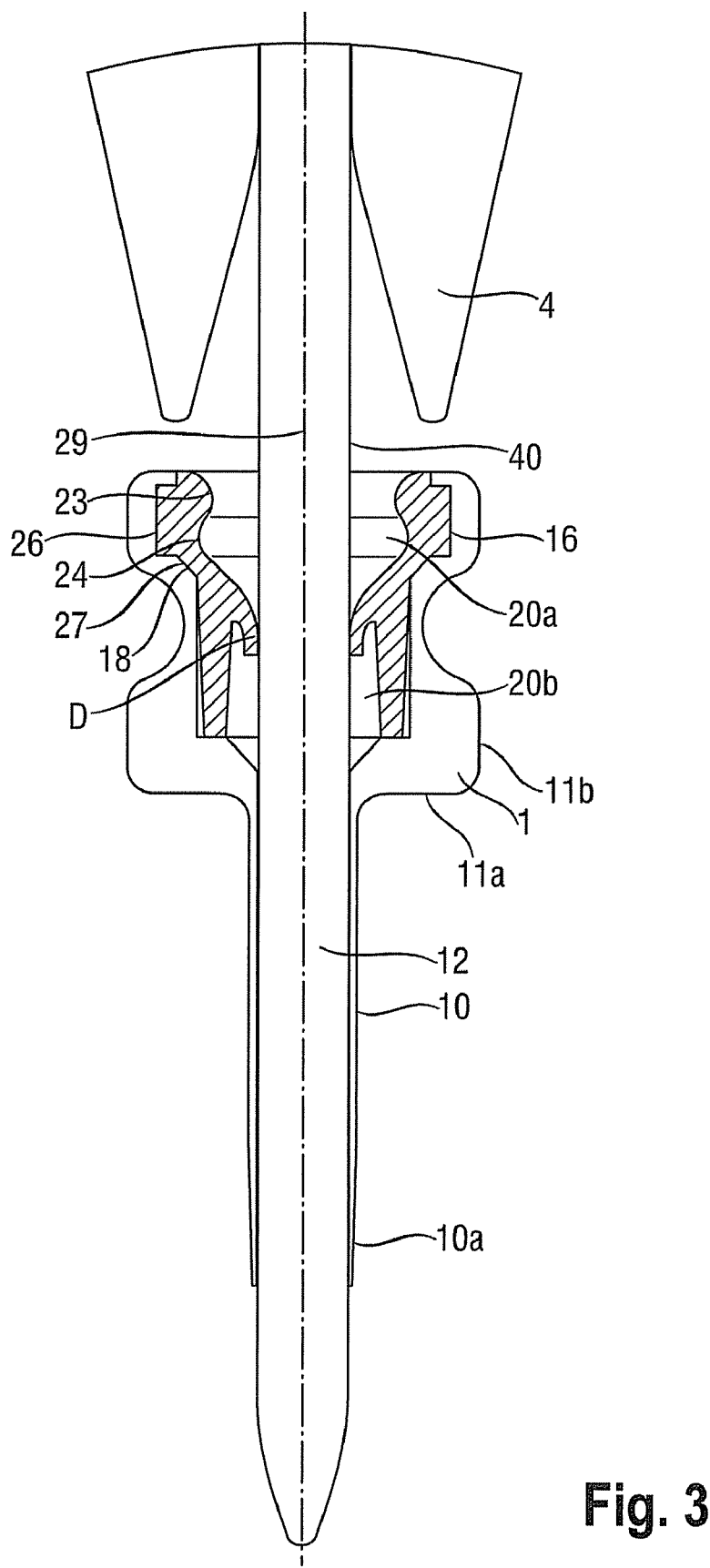
FIG. 3 shows a cross-sectional view of the trocar with the seal according to FIG. 1, and with an instrument.

FIG. 3 shows an instrument 4 which is connected to the trocar 1 and to the seal 2. The instrument 4, for example a light source or a cutting instrument, is shown here with a cylindrical rod or mandrel 40. In analogy with the connection described above, the instrument 4 with the mandrel 40 is pushed along its centre axis into the trocar 1 and seal 2. In so doing, the mandrel 40, like the attachment tube 31, penetrates the seal membrane 21 or seal opening 22. A leaktight contact is again achieved between the seal opening 22 and the surface of the mandrel 40. Moreover, the instrument 4 can be moved with a slight force along the centre axis, without negatively affecting the sealing action between the mandrel 40. The mandrel 40 can, for example, be a 23-gauge mandrel. Alternatively, the mandrel 40 can also be a 25-gauge mandrel or a 20-gauge mandrel. That is to say, the trocar 1 and the seal 2 can receive 20-gauge, 23-gauge and 25-gauge instruments. Other diameters are likewise conceivable.

As soon as the infusion attachment 3 or the instrument 4 is removed from the trocar 1 and from the seal 2, the seal membrane 21 or seal opening closes on account of the elastic properties of the seal membrane 21. This is particularly advantageous, since no fluids can escape from the eye after removal of the instruments 3, 4.

Figure 5A:
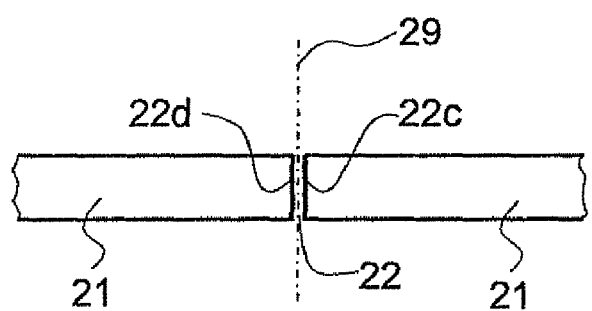
FIGS. 5a and 5b show a schematic cross-sectional view of the seal membrane, the cross-section being taken along the centre axis.

It is clear from FIGS. 3 and 5a that the underside of the curved seal membrane 21 is flat and extends perpendicular to the boundary surfaces of the seal membrane 21 itself. In other words, this means that the slit or the slits of the seal opening 22 extend substantially perpendicular to the surface of the seal membrane 21, that is to say parallel to the centre axis 19, 29. The two side walls 22c and 22d of the slits are accordingly perpendicular to the surface of the seal membrane 21.

Figure 5B:
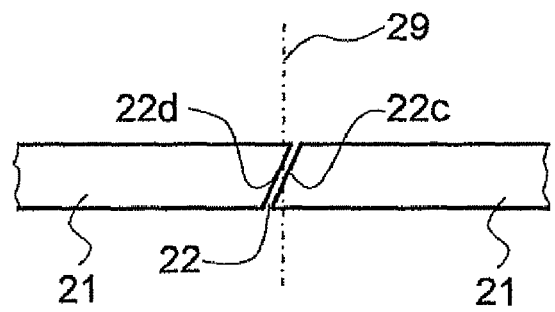

In other illustrative embodiments, as shown in FIG. 5b, it would also be possible for the slit or slits of the seal opening 22 to be at an angle to the axis 19, 29. The side walls 22c and 22d are accordingly at an angle to the centre axis 19, 29 and at an angle to the surface of the seal membrane 21.

The invention claimed is:

1. A kit, said kit comprising a trocar and an instrument which is designed for ophthalmology and can be guided through a trocar comprising
    said trocar, which comprises a cannula with a centre axis, a flange formed integrally on this cannula, an opening extending along the centre axis through the cannula, and a receiving opening that extends along the centre axis through the flange, said opening and said receiving opening forming an opening that runs all the way through the trocar, wherein a seal is arranged in the receiving opening of the trocar, wherein said seal comprises:
    a seal element, having a seal opening, a first side and a second side;
    an instrument opening, which instrument opening extends along a centre axis on said first side and said second side of the seal element all the way through the seal; and
    a clamping element for establishing a form-fit connection to an instrument that is inserted at least partially into the instrument opening and through the seal opening; wherein
    said instrument comprises a clamp section that is complementary to said clamping element, wherein said clamping element or the instrument or both being designed in such a way that they can be compressed during insertion of the instrument into the seal and such that the original shape of these parts can be recovered when a predefined depth of insertion is reached, such that the surface of said clamping element is in contact with the surface of the complementary section of the instrument, such that a form-fit connection is established between said clamping element of said seal and said clamp section of said instrument.

2. The kit according to claim 1, wherein the complementary section of the instrument has the shape of a groove which extends about a complete or partial circumference and into which a bead of said seal of said clamping element engages.

3. The kit according to claim 1, wherein the complementary section of the instrument has the shape of a bead which extends about a complete or partial circumference and which can be received by a groove arranged on said clamping element.

4. The kit according to claim 1, wherein said clamping element is designed in one piece with the seal.

5. The kit according to claim 1, wherein the seal element is a membrane which extends substantially perpendicular to the centre axis of the seal, and the seal opening comprises at least one slit.

6. The kit according to claim 1, wherein said clamping element is arranged before the seal element, seen in the direction of insertion of an instrument.

7. The kit according to claim 1, wherein said clamping element is designed as a circumferential clamping bead, which reduces the diameter of the instrument opening.

8. The kit according to claim 1, wherein said clamping element is designed as a clamping bead divided into sections, at least three clamping bead sections being formed which reduce the diameter of the instrument opening.

9. The kit according to claim 1, wherein said clamping element is designed as a groove extending about a complete circumference or as a groove divided into sections.

10. The kit according to claim 1, wherein the seal comprises a circumferential flange on its outer face.

11. The kit according to claim 1, wherein the receiving opening comprises a circumferential groove in which a circumferential flange of the seal engages in order to establish a form-fit connection between trocar and seal.

12. The kit according to claim 1, wherein the seal is injected directly into the receiving opening of the trocar by a plastics injection-moulding technique.

13. The kit according to claim 1, wherein the outer circumferential surface of the seal faces and is in contact with the circumferential surface of the opening in the trocar.

14. The kit according to claim 1, wherein the trocar and the seal are produced in one piece from a plastic.

* * * * *